(12) United States Patent
Geist et al.

(10) Patent No.: US 7,771,350 B2
(45) Date of Patent: Aug. 10, 2010

(54) LARYNGOSCOPE AND LARYNGOSCOPE HANDLE APPARATUS INCLUDING AN LED AND WHICH MAY INCLUDE AN ERGONOMIC HANDLE

(75) Inventors: Leroy D. Geist, Parker, CO (US); Leroy D. Jutte, Highlands Ranch, CO (US)

(73) Assignee: General Electric Company, Schenectady, NY (US)

( * ) Notice: Subject to any disclaimer, the term of this patent is extended or adjusted under 35 U.S.C. 154(b) by 1298 days.

(21) Appl. No.: 11/255,323

(22) Filed: Oct. 21, 2005

(65) Prior Publication Data

US 2007/0093693 A1 Apr. 26, 2007

(51) Int. Cl.
*A61B 1/267* (2006.01)
(52) U.S. Cl. .................................... 600/199; 600/185
(58) Field of Classification Search ......... 600/199–200; 362/202–208
See application file for complete search history.

(56) References Cited

U.S. PATENT DOCUMENTS

| 3,050,049 | A | * | 8/1962 | Kruglick | .................... 600/200 |
| 4,211,955 | A | | 7/1980 | Ray | |
| 4,384,570 | A | | 5/1983 | Roberts | |
| 4,727,289 | A | | 2/1988 | Uchida | |
| 4,815,451 | A | * | 3/1989 | Bauman | .................... 600/198 |
| 5,097,180 | A | | 3/1992 | Ignon et al. | |
| 5,559,422 | A | | 9/1996 | Fahrenkrug | |
| 6,102,851 | A | | 8/2000 | Mellin | |
| 6,277,068 | B1 | * | 8/2001 | Wojnowicz et al. | ......... 600/199 |
| 6,547,394 | B2 | | 4/2003 | Doherty | |
| 6,974,234 | B2 | * | 12/2005 | Galli | .......................... 362/294 |
| 2003/0210552 | A1 | | 11/2003 | Barlin | |
| 2004/0122292 | A1 | | 6/2004 | Dey et al. | |
| 2004/0145891 | A1 | | 7/2004 | Heine et al. | |
| 2004/0183482 | A1 | | 9/2004 | Roberts et al. | |
| 2005/0057187 | A1 | * | 3/2005 | Catalano | ..................... 315/291 |

FOREIGN PATENT DOCUMENTS

| EP | 1433423 A2 | 6/2004 |
| JP | 2005046565 | 2/2005 |
| WO | WO 03/071352 A1 | 8/2003 |

OTHER PUBLICATIONS

Fraen Srl Maximizing Light,6 pages,US,Jul. 22, 2005.
X-Lite Compact,Rusch,1 page,no date.
X-Lite Take Apart,Rusch,1 page,no date.
Beta Fo Laryngoscope Blade Handle System,Heine,1 page,no date.
Standard Laryngoscope Handles,Heine,no date,1 page.
Fiber Optic Laryngoscope Handles,Welsh-Allen, 3 pages,Jul. 1996.

* cited by examiner

*Primary Examiner*—Eduardo C Robert
*Assistant Examiner*—Elana B Fisher
(74) *Attorney, Agent, or Firm*—Alan Taboada; Mosier IP Law Group

(57) ABSTRACT

A laryngoscope including a laryngoscope blade and laryngoscope handle apparatus including an LED and which may include an ergonomic handle and laryngoscope handle apparatus including an LED and which may include an ergonomic handle.

28 Claims, 14 Drawing Sheets

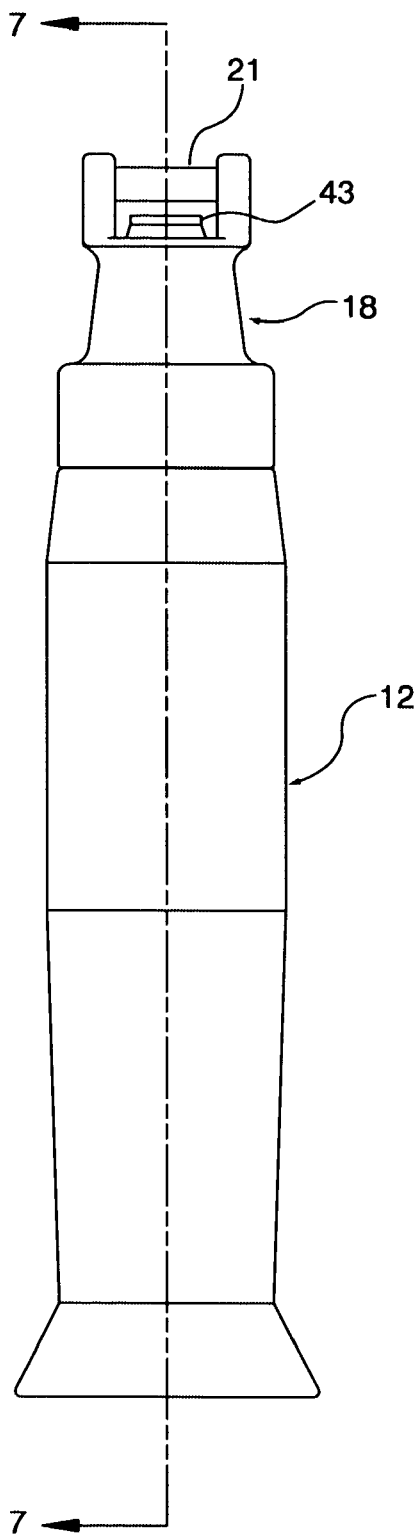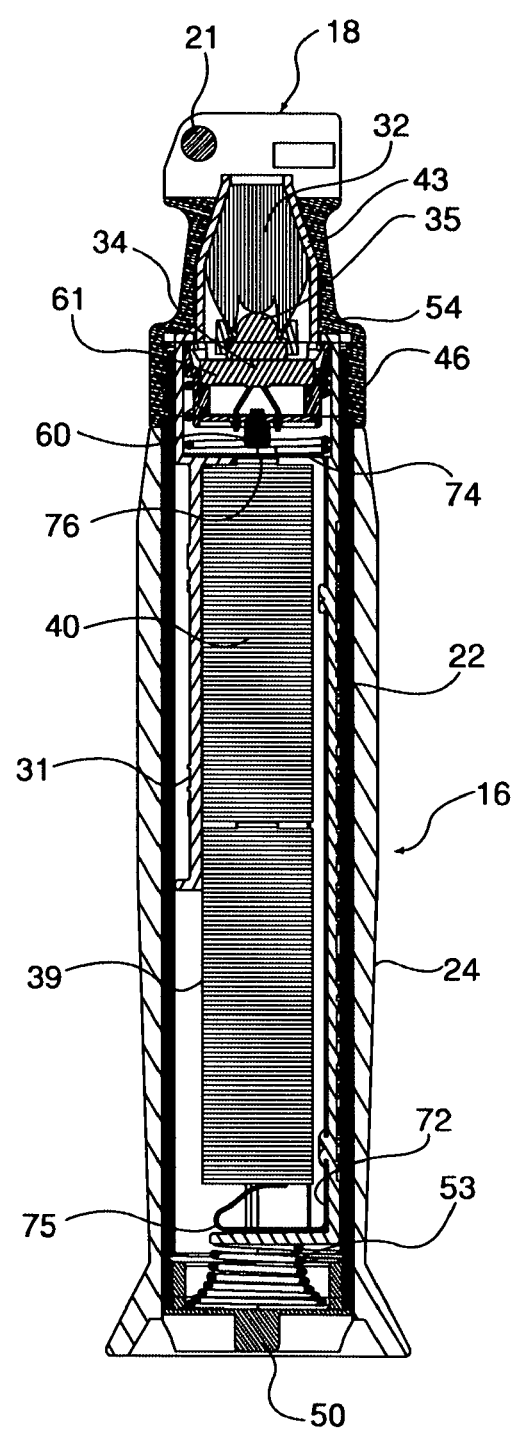
FIG. 6
FIG. 7

LARYNGOSCOPE AND LARYNGOSCOPE HANDLE APPARATUS INCLUDING AN LED AND WHICH MAY INCLUDE AN ERGONOMIC HANDLE

BACKGROUND OF THE INVENTION

Field of the Invention

This invention relates generally to a laryngoscope including a laryngoscope blade and laryngoscope handle apparatus including an LED and which may include an ergonomic handle and further relates to laryngoscope handle apparatus including an LED and which may include an ergonomic handle.

As is well known a laryngoscope is used to insert an endotracheal tube through the mouth and throat and into the trachea of a patient. Such laryngoscope typically includes a blade mounted removably and pivotally to a laryngoscope handle and the blade is used to move the tongue and epiglottis out of the way to allow insertion of the endotracheal tube into the trachea for proper tracheal intubation. To assist in the insertion of the endotracheal tube, the typical laryngoscope handle includes a light source for directing light outwardly toward the blade, which is typically provided with an optical fiber extending along its length, and the light is transmitted through the optical fiber into the mouth and throat of the patient to assist in tracheal intubation.

More particularly, the typical laryngoscope handle includes a head portion for removably and pivotally engaging the blade and a hollow handle containing batteries, a light source such as a halogen or xenon bulb, batteries, electrical contacts for placing the batteries in communication with the light source and a switching mechanism that switches the light source on when the blade is mounted to the head and pivoted for tracheal intubation.

The typical bulbs operate at 2.5V to 3.5V and produce a yellow-white light with a color temperature of 3,000 K to 3,500 K and an initial brightness of 45 to 50 lumens. The typical battery life from AA size batteries is approximately 2.5 hours and the typical battery life from C size batteries is approximately 3.5 hours. As the batteries discharge, the brightness from the bulb continuously decreases. The practical battery life, before the bulb is too dim to use, therefore, is typically only about 1 to 1.5 hours. The expected life of the bulb is 4 to 12 hours, and the bulbs easily break, or fail to work if the laryngoscope handle is subject to impact such as being dropped on a floor.

The grip portion of the typical laryngoscope handle is a straight metallic cylinder with a knurled surface. Laryngoscope handles are known which use an LED as the light source.

SUMMARY OF THE INVENTION

A laryngoscope including a laryngoscope blade and laryngoscope handle apparatus including an LED and which may include an ergonomic handle and laryngoscope handle apparatus including an LED and which may include an ergonomic handle.

DESCRIPTION OF THE DRAWINGS

FIG. 6 is a vertical external view of the first embodiment of the laryngoscope handle apparatus of the present invention;

FIG. 7 is a vertical cross section of a laryngoscope handle apparatus of FIG. 6 taken generally along the line 7-7 and in the direction of the arrows;

DETAILED DESCRIPTION

Figures 1, 2:
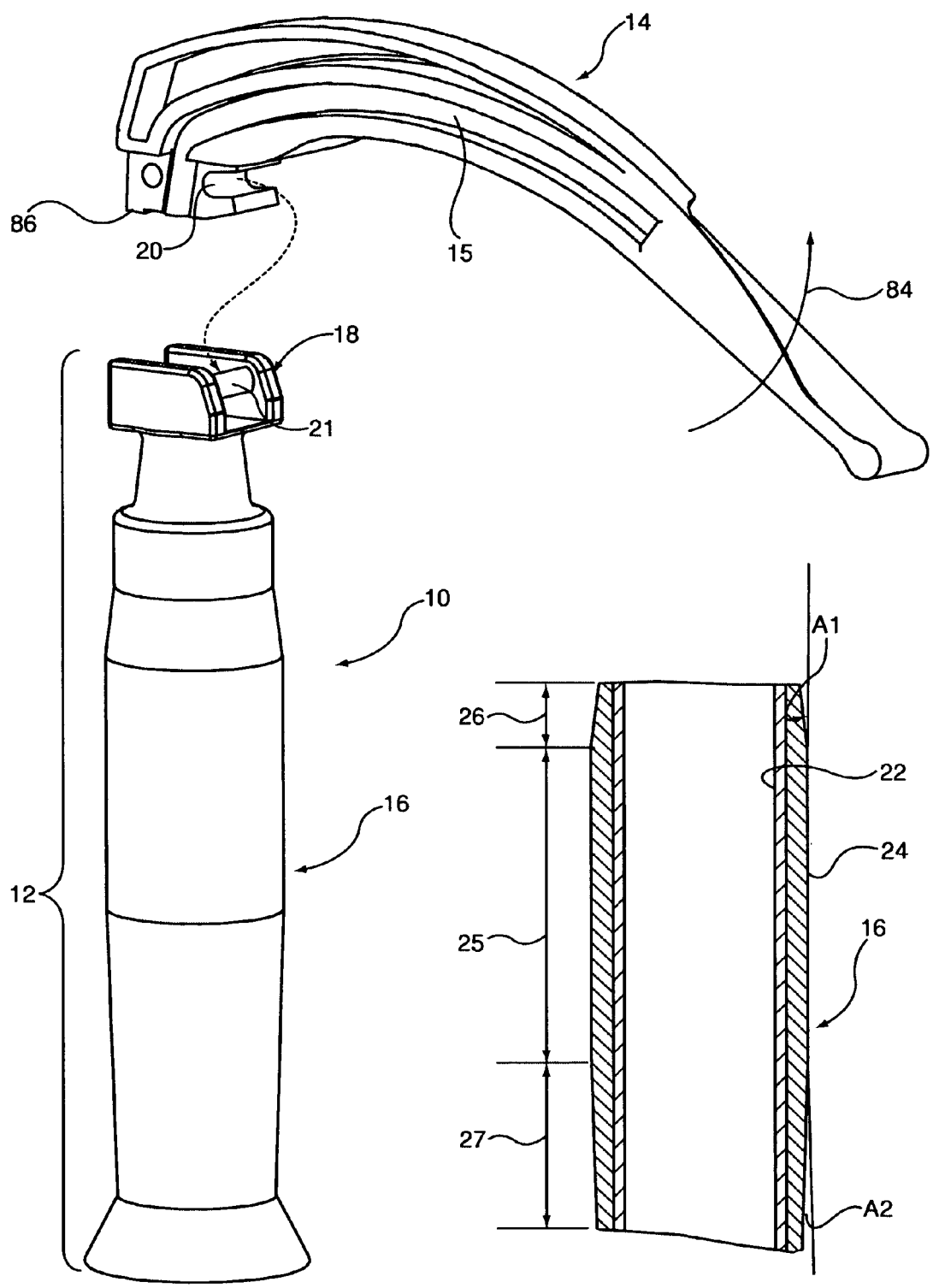
FIG. 1 is a perspective view of a first embodiment of a laryngoscope of present invention, a first embodiment of a laryngoscope handle apparatus of the present invention, a laryngoscope blade and illustrates the mounting of the laryngoscope blade to the laryngoscope handle apparatus.
FIG. 2 is a diagrammatical cross-sectional illustration of the laryngoscope handle of FIG. 1.

The first embodiment of a laryngoscope embodying the present invention, and for providing illuminated tracheal intubation, is shown in FIG. 1 and indicated by general numerical designation 10. The laryngoscope 10 includes laryngoscope handle apparatus, indicated by general numerical designation 12, and a laryngoscope blade of a type known to the art indicated by general numerical designation 14, and in which an optical fiber 15 is mounted in the manner known to the art. The laryngoscope handle apparatus 12 includes an ergonomic laryngoscope handle, indicated by general designation 16, and a head, indicated by general numerical designation 18, mounted to the upper end of the ergonomic handle 16. The laryngoscope blade 14 is provided with an inwardly curved surface 20 for engaging the cylindrical rod 21 provided at the top of the head 18 in the manner known to the art and as indicated by the dashed line in FIG. 1, to mount the laryngoscope blade 14 removably and pivotally to the head 18 and to the laryngoscope handle apparatus 12.

Referring to FIG. 2, the ergonomic laryngoscope handle 16 includes a hollow rigid inner cylinder 22 and a generally cylindrical outer soft layer of material 24 molded around the rigid inner cylinder, in a manner known to the art, and having a durometer of about 55 on the Shore A scale. The layer of soft material 24 includes a generally central portion 25 having a uniform diametrical cross-section, a first outer portion 26, or upper portion as oriented in FIG. 2, varying in diametrical cross-section and tapering inwardly at a taper angle A1, and a second outer portion 27, or lower portion as oriented in FIG. 2, varying in diametrical cross-section and tapering inwardly at a taper angle A2 smaller then the taper angle A1. In the preferred embodiment the angle A1 was about six degrees and the angle A2 was about two degrees. The rigid inner cylinder 22 may be a hollow aluminum cylinder and the layer of soft material 24 may be a thermoplastic vulcanizate, a synthetic thermoplastic rubber such as Santoprene 281-55MED available from the Advanced Elastomer Systems Corporation located in at 388 South Main Street, Akron, Ohio.

The term ergonomic handle as used herein and in the appended claims means a handle which provides improved surface area contact between the handle and the hand gripping the handle, which positions the muscles of the hand gripping the handle near the resting position for optimal use of force and control and which minimizes the pressure against the regions of the hand gripping the handle which gripping can cut off circulation to the tissues of the hand. Such ergonomic handle reduces hand fatigue resulting from use of the handle.

Figure 3:
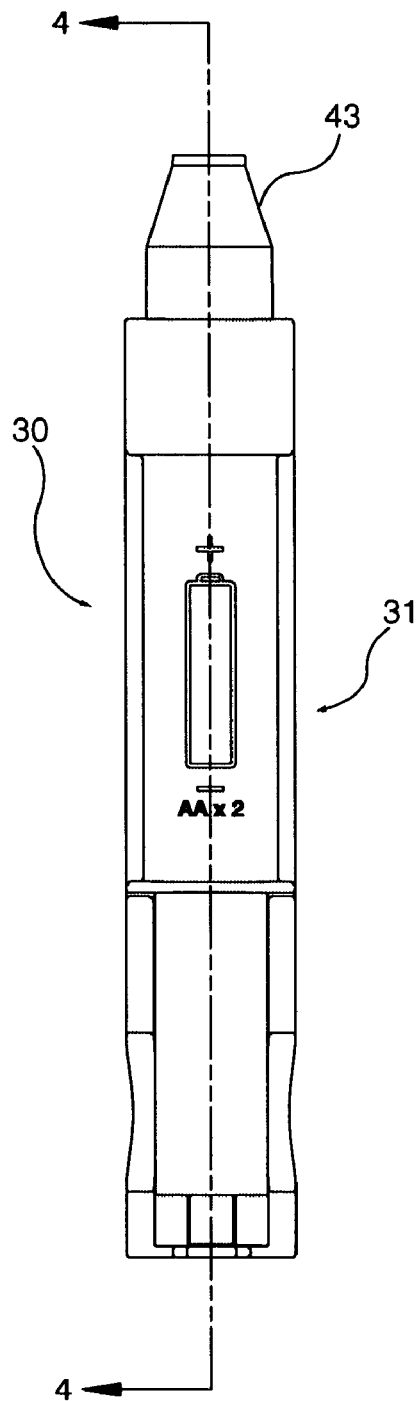
FIG. 3 is an external vertical view of an LED/battery/lens pack utilized in the first invention embodiments.
Figure 4:
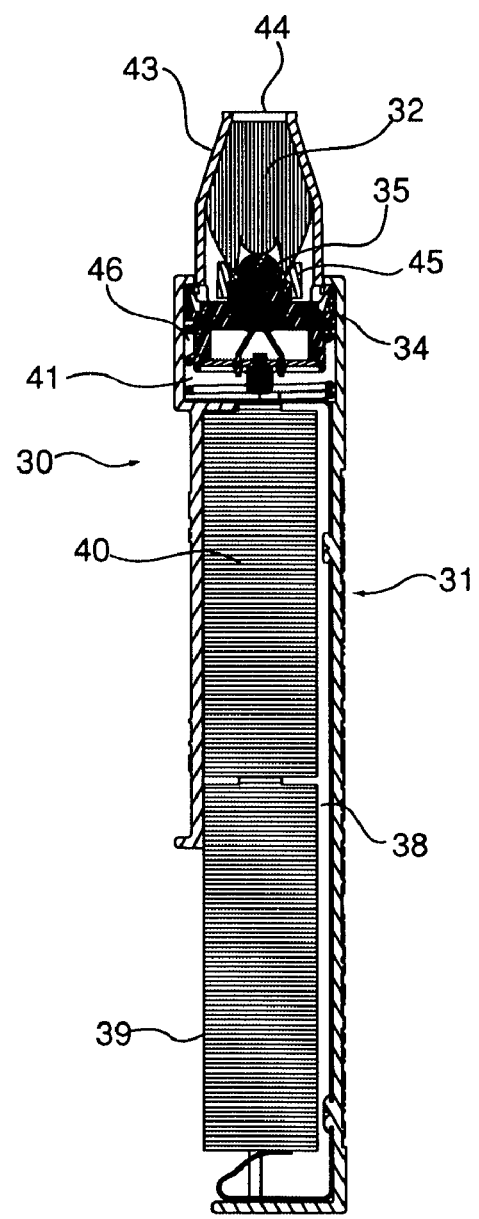
FIG. 4 is a vertical cross-sectional view taken generally along the line 4-4 in FIG. 3 and in the direction of the arrows.
Figures 8, 8A, 8B:
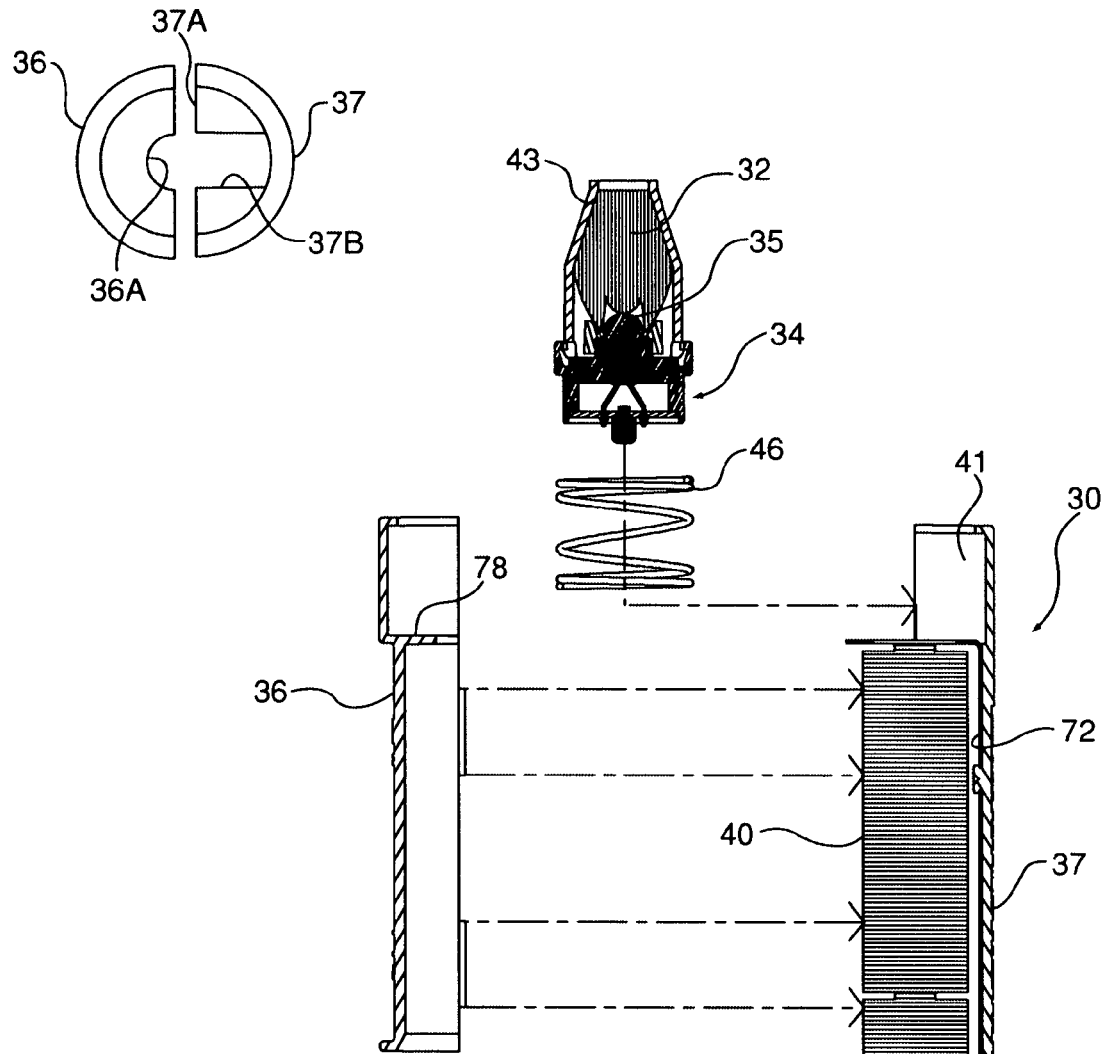
FIG. 8 is a diagrammatical illustration, partially in cross section, illustrating the assembly of the module, lens, lens cover, compression spring and DC batteries to the case or casing and showing the casing as initially formed in two halves or sections.
FIG. 8A is a top view of the case sections 36 and 37 shown in FIG. 8.
FIG. 8B is a top view of the case sections 36 and 37 assembled and mounted together.

Referring now to FIGS. 3 and 4, the laryngoscope 10, and the laryngoscope handle apparatus 12, includes an LED/battery/lens pack indicated by general designation 30. The pack 30, FIG. 4, includes a casing indicated by general numerical designation 31, a lens 32 and a module indicated by general numerical designation 34; the module 34 includes an LED 35 and is shown in detail in FIG. 11 and described in detailed below. The casing 31 is generally cylindrical, may be made by injection molding and from a suitable thermoplastic such as Acronitrile Butadiene Styrene (ABS), and is made in two halves or casing sections 36 and 37 as shown in FIG. 8. The casing 31 provides a lower chamber 38 for receiving a pair of serially connected batteries 39 and 40 which are inserted into the chamber 38 through the opening provided in the lower left portion of the casing 31 shown in FIG. 4. The casing 31 further provides a chamber 41 for receiving, generally, the module 34. The pack 30 further includes a lens cover 43 in which the lens 32 is mounted and which cover is mounted to the module 34 as described and detailed below. The lens cover 43 provides an opening 44 at the top through which light from LED 35 is transmitted to and through the lens 32. As shown in FIG. 4, the upper portion of the lens cover 43 is complementary in shape to the upper portion of the lens 32. A generally annular lens spacer 45 may be included to locate the lens 32 relative to the LED 35 in an optically correct position in the manner known to the art. The lens 32 may be a total internal reflection collector made of suitable transparent material and shaped to internally reflect and transmit light emitted by the LED 35. The lens 32 is sometimes referred to in the art as a light injector and may be a Fraen Fiber Light Injector (FFLI) available from the Fraen Corporation, 80 New Crossing Road, Reading, Pa. The pack 30 further includes an electrically conductive compression spring 46, better seen in FIG. 8, which, it will be generally understood, biases the module 34 upwardly in the casing chamber 41. In the preferred embodiment, the batteries, DC energy source 39 and 40 are two M batteries.

Figure 5:
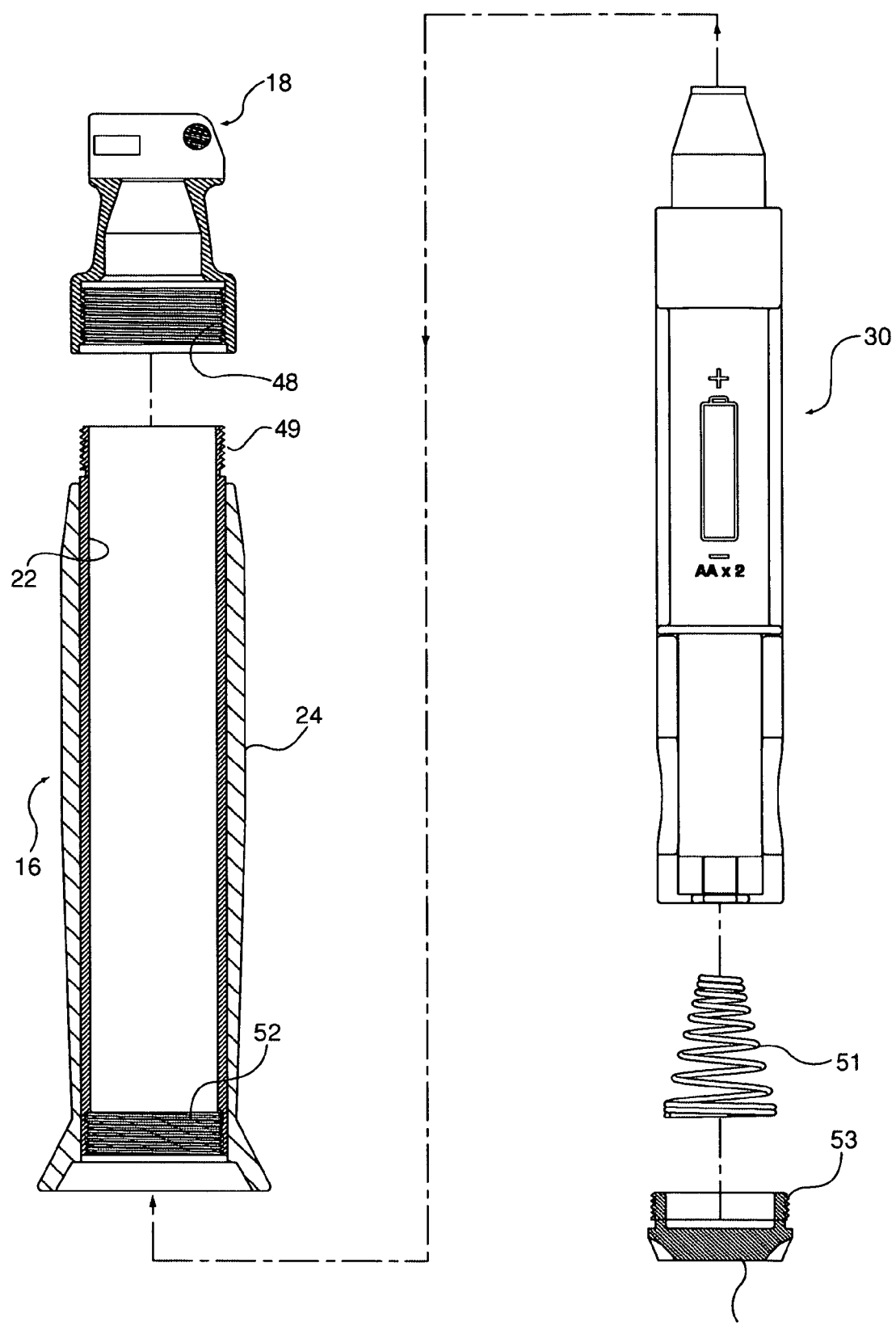
FIG. 5 is an exploded diagrammatical illustration, partially in cross-section, illustrating the mounting of the head and the LED/battery/lens pack to the laryngoscope handle.

The assembly of the head 18, ergonomic laryngoscope handle 16, and LED/battery/lens pack 30 is illustrated in FIG. 5. The lower part of the head 18 is provided with internal threads 48 which threadedly engage the external threads 49 provided on the upper portion of the inner rigid cylinder 22 to mount the head to the handle. The LED/battery/lens pack 30 is inserted upwardly into the handle 16 from the bottom or base as indicated by the dash lines and arrows in FIG. 5 and an end cap 50 and spring 51 hold the LED/battery/lens pack 30 in position in the handle 16, more particularly, the lower portion of the cylinder 22 is provided with internal threads 52 which are threadedly engaged by the external threads 53 provided on the end cap 50 to mount the pack 30 in the handle 16. An external view, or outline view, of the head 18 mounted to the ergonomic laryngoscope handle 16, having the LED/battery/lens pack 30 mounted therein is shown in FIG. 6; a vertical cross-section view of this assembly is shown in FIG. 7.

The detailed structure of the LED/battery/lens pack 30 and the electrical connections between the batteries 39 and 40, and the module 34 are illustrated in FIG. 8-12. As will be understood from FIG. 8, the electrically conductive compression spring 46 is mounted to the module 34 and these elements, and the lower portion of the lens cover 43, are inserted into the rightward portion of the chamber 41 provided by the casing section 37, and the elongated negative conductor 72, better seen in FIGS. 9 and 10 and described in detail below, is placed in the casing section 37, after which the casing section 36 is placed in engagement with the casing section 37 and the sections 36 and 37 are suitably mounted together, permanently, such as by a suitable adhesive or by solvent or by ultrasonic welding.

Figure 11:
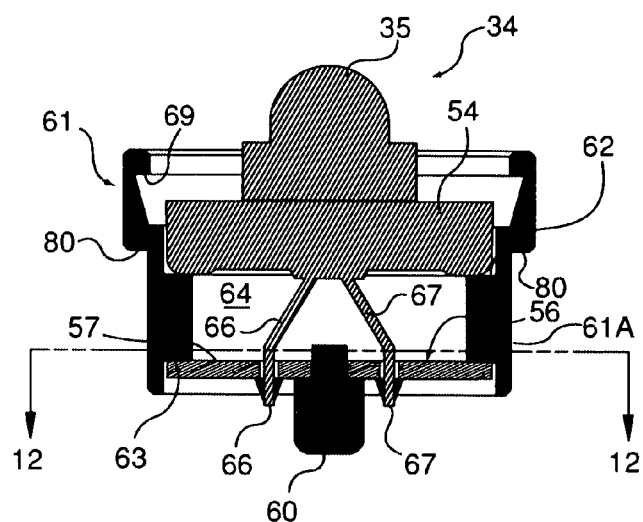
FIG. 11 is a diagrammatical vertical cross-sectional view of a first module including an LED and printed circuit board containing an LED drive circuit used in the first laryngoscope and first laryngoscope handle apparatus invention embodiments.

The module 34, FIG. 11, includes the LED 35 which is mechanically and electrically mounted to a printed circuit board 54 which contains an LED drive circuit, or LED driving circuit, (not separately shown). The LED 35 and LED drive circuit contained in the printed circuit board 54 are substantially the same as shown and described in United States Patent Application Publication No. U.S. 2005/0057187 A1, published Mar. 17, 2005, entitled Universal Light Emitting Illumination Device and Method, Anthony Catalano, Inventor.

This United States Patent Application Publication is hereby incorporated herein by referenced as fully reproduced herein and is referred to hereinafter as the Catalano reference. More particularly, this Catalano reference note particularly, FIG. 10 and its associated written description, shows and describes the LED drive circuit or LED drive circuitry, for receiving DC voltage and producing and applying constant current to the LED to cause the LED to emit light. The LED 35 and printed circuit board 54 containing the LED drive circuit are available from TERRALUX, 1501 Lee Hill Road, Boulder, Colo. Referring further to FIG. 11, the module 34 includes another printed circuit board indicated by General American Designation 56 made of suitable electrical insulating material and which includes a top surface 57 on which electrical conductors, or electrical traces, 58 and 59 are suitably formed or deposited in the manner known to the art. The module 34 includes an electrically conductive positive battery contact 60, suitably mounted mechanically to the printed circuit board 56, and electrically connected to the electrical trace 58, such as by soldering as will be understood particularly from FIG. 12. The module 34, referring again to FIG. 11, includes a generally annular heat sink 61 made of suitable heat dissipating and electrically conducted material, such as aluminum, and which heat sink provides an upper inner annular shoulder 62 and a lower inner annular shoulder 63 separated from the first inner annular shoulder by a cylindrical opening 64. As shown in FIG. 11, the bottom service of the printed circuit board 54 includes an outer annular portion residing on the inward annular shoulder 62 and the printed circuit board 56 includes a top surface having an outer annular portion residing on the inward annular shoulder 63.

Figure 12:
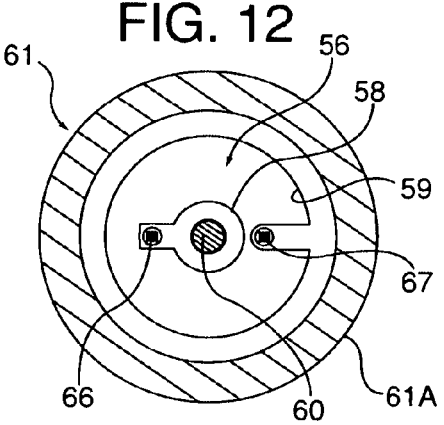
FIG. 12 is a view taken generally along the line 12-12 in FIG. 11 and in the direction of the arrows.

The printed circuit board 54, FIG. 11, includes a positive lead 66 and a negative lead 67 connected to the LED drive circuit contained in the printed circuit board 54. The positive lead 66 extends downwardly through the cylindrical opening 64 and into and through a hole formed in the printed circuit board 56 with the positive lead 66 being mounted mechanically to the printed circuit board 56 and electrically to the electrical trace 58, note FIG. 12, such as by soldering; the electrical trace 58 also electrically interconnects the positive lead 66 and the positive battery contact 60 as shown in FIG. 12. The negative lead 67 from the printed circuit board 54, FIG. 11 extends downwardly through the cylindrical opening 64 and through a hole formed in the printed circuit board 56 with the negative lead 67 being mounted mechanically to the printed circuit board 56 and electrically to the electrical trace 59 as shown in FIG. 12 such as by soldering. It will be understood from FIGS. 11 and 12 that the lower annular portion 61A of the heat sink 61 is in engagement with the electrical trace 59, and since as described above the heat sink 61 is electrically conductive, the electrical trace 59 places the heat sink 61 in electrical contact with the negative lead 67 and thereby to the LED drive circuit contained in the printed circuit board 54.

Figure 12A:
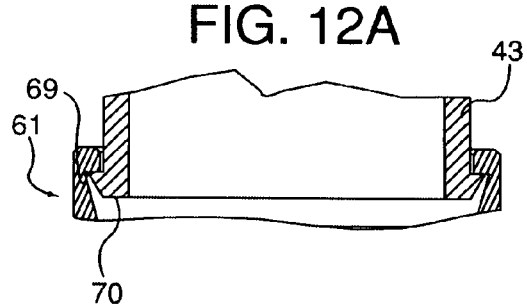
FIG. 12A is a partial view of a diagrammatical illustration of the mounting of the lens cover to the heat sink of the module shown in FIG. 11.

As is further shown in FIG. 11, the upper portion of the heat sink 61 is provided with an inward annular lens cover seating or latching surface 69 which is used to latch the lens cover 43, FIGS. 4 and 8, to the heat sink 61. The lens cover 43 may be made suitably, such as by injection molding, and of a suitable resilient plastic material, such as ABS and includes an outwardly extending lower annular ring or shoulder 70, FIG. 12A which, as shown in FIG. 12A, is latched underneath the heat sink seating shoulder 69 to snap-fit the lens cover 43 to the heat sink 61 and thereby mount the lens cover 43 and the lens 32 to the heat sink 61, this also mounts the lens 32 to the LED 35 as shown FIGS. 4, 7 and 8.

Figure 9:
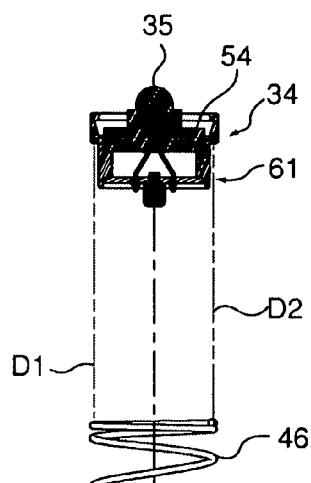
FIG. 9 is a diagrammatical assembly view illustrating the assembly of the module, compression spring, and negative conductor to the batteries or DC energy source.
Figure 10:
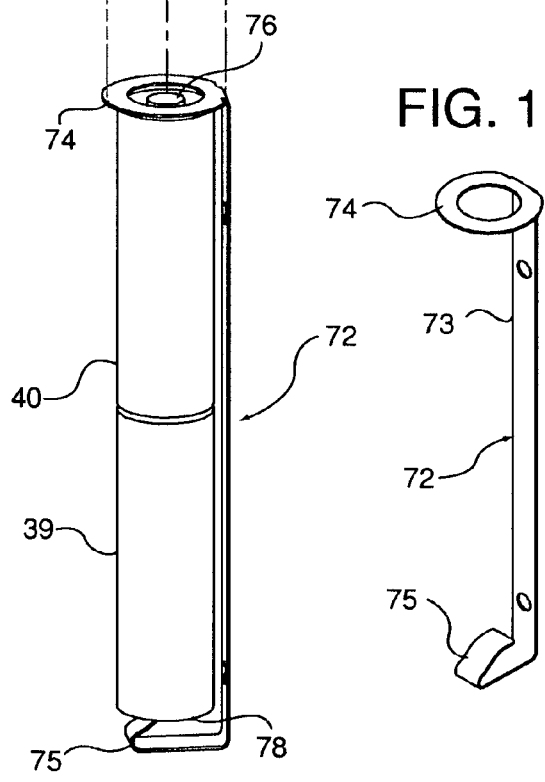
FIG. 10 is a perspective view of the negative conductor included in the first laryngoscope handle invention embodiment.

Referring further to the electrical interconnections between the module 34 and the batteries 39 and 40, and referring to FIGS. 8, 8A, 9 and 10, the LED/battery/lens pack 30 includes an elongated negative electrical conductor indicated by general numerical designation 72 in FIGS. 9 and 10. The negative conductor 72 may be made of suitable electrically conducted material such as brass and may be made suitability, such as by stamping. The negative electrical conductor 72, particularly FIGS. 9 and 10, includes an elongated potion 73 and an upper annular portion 74 disposed or bent perpendicularly to the elongated portion 73. The annular portion 74, as will be noted particularly from FIG. 9, circles, resides over and is spaced from the positive battery terminal 76 shown in FIG. 9 so as not to electrically connect to the positive battery terminal 76. Referring to FIG. 8A the case or casing section 36 is provided with an inward outwardly extending generally C-shaped member 36A and the case section 37 is provided with two inward outwardly extending members 37A and 37B, and upon the case sections being assembled and mounted together, as described above and as shown in FIG. 8B, the members combine to form a generally C-shaped inner seating shoulder 37C. The outer portion of the annular portion 74 of the negative conductor 72 resides on, and is supported by, the seating shoulder 37C in the casing 31 as will be generally understood from FIG. 7. Referring again to FIGS. 9 and 10, the lower portion 75 of the negative conductor 72 is bent or formed inwardly on itself to provide a spring portion which mechanically engages the negative terminal 78 of the battery 39, note FIG. 9, and which spring portion 75 biases or forces the batteries 39 and 40 upwardly in the lower case chamber 38 as will be understood from FIG. 8.

Referring again to FIG. 11, the heat sink 61 is provided with an outer annular compression spring seating shoulder 80 which engages and seats the upper portion of the spring 46, as shown in FIG. 9. Accordingly it will be understood from the dashed lines D1 and D2 in FIG. 9, that the upper portion of the electrically conducted compression spring 46 mechanically and electrically engages the lower annular portion 61A of the heat sink 61, and that the lower portion of the spring 46 resides on and thereby mechanically and electrically engages the annular portion 74 of the negative conductor 72. It will be further understood from FIG. 9 that the negative terminal 78 of the battery 39 is normally electrically connected to the LED drive circuit provided in the printed circuit board 54 through the negative electrical conductor 72, the lower spring portion 75 of which directly engages the battery negative terminal 78, and the upper annular portion 74 of the negative electrical conductor 72 which is in mechanical and electrical engagement with the electrically conductive compression spring 46 which is in mechanical and electrical engagement with the heat sink 61 which in turn is a mechanical and electrical engagement for the negative electrical trace 59, FIG. 12 which in turn is an electrical and mechanical engagement with the negative lead 67, FIG. 11, which is connected electrically to the LED drive circuit contained in the printed circuit board 54, FIG. 11. Thus it will be understood, and referring also to the vertical cross-sectional assembly view of FIG. 7, that the negative battery terminal 78 is normally connected through the forgoing described negative electrical connection to the LED drive circuit contained in the printed circuit board 54 As will be further understood from FIG. 7, the electrically conductive compression spring 46 acting between the annular portion 74 of the negative conductor 72 and heat sink annular shoulder 80, FIG. 11, normally biases the module 34, the lens 32 and the lens cover 43, upwardly is viewed in FIG. 7, and normally maintains the positive battery contact 60 FIG. 11, out of engagement with the positive terminal 76, FIG. 9 of the battery 40.

Figure 13:
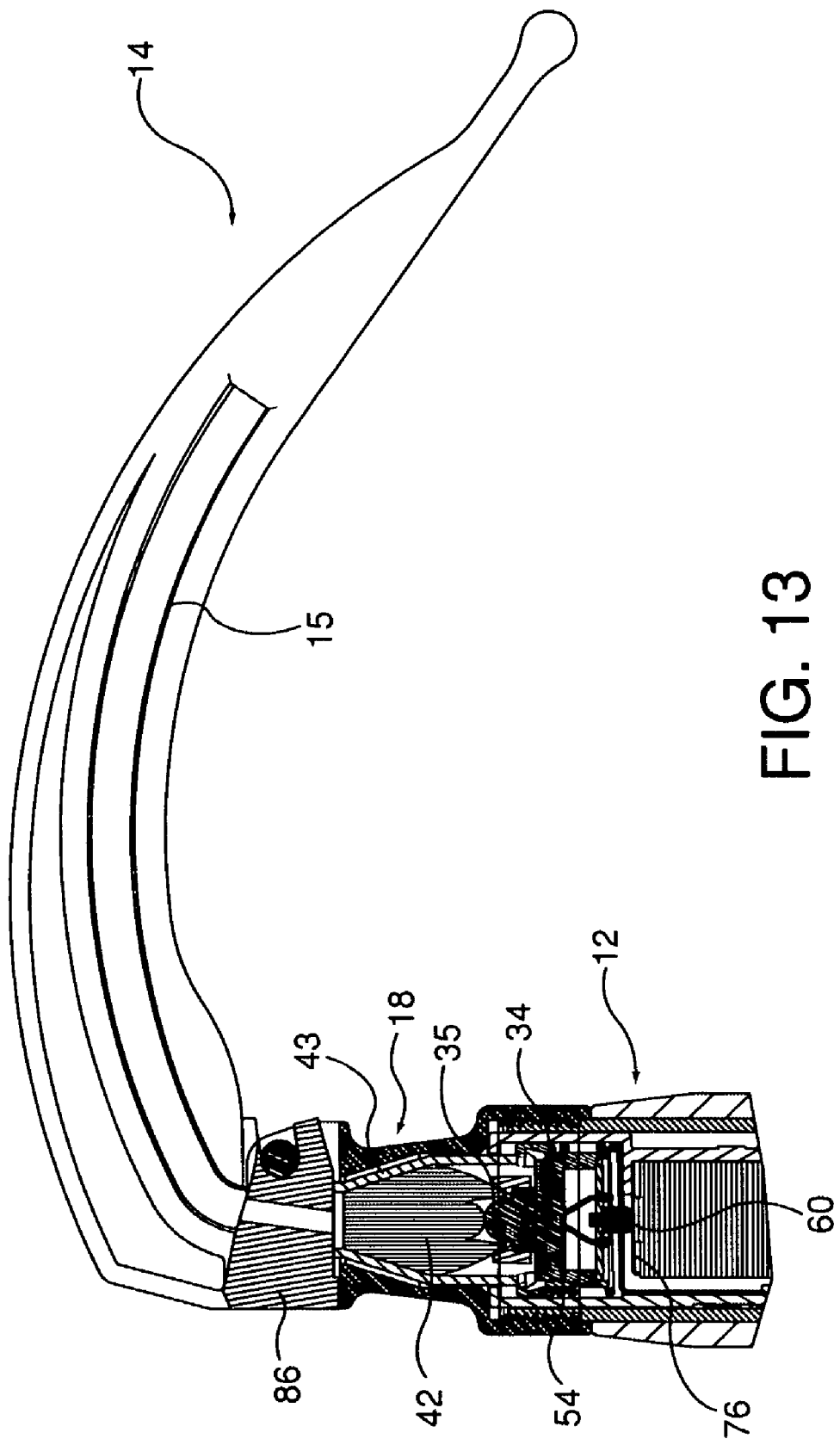
FIG. 13 is a partial cross-sectional view of the upper portion of the first laryngoscope invention embodiment showing the laryngoscope blade pivoted for tracheal intubation and illustrating the manner in which the base of the blade engages the lens cover and forces it downwardly to complete the circuit between the DC energy source and the LED drive circuit for energizing the LED and providing illuminated tracheal intubation.

Referring to FIG. 13, it will be understood that upon the Laryngoscope blade 40 being mounted to the head 18 as described above and indicated by the in FIG. 1, and upon the Laryngoscope blade 14 being pivoted upwardly for tracheal intubation as indicated by the curved arrow 84 in FIG. 1, the base 86 of the Laryngoscope blade 14, FIG. 13 is pivoted into engagement with the lens cover 43 and forces the lens cover, lens 42 and module 34 downwardly causing the positive battery contact 60, to pass through the negative conductor annular portion 74, FIG. 9, and engage the positive battery contact 76, FIG. 9, thereby completing the positive electrical connection to the LED drive circuit contained in the printed circuit board 54. Upon the positive and negative terminals of the batteries 34 and 40 being connected to the LED drive circuit contained in the printed circuit board 54, the DC voltage is applied to the LED drive circuit which produces constant current, as described in the incorporated Catalano reference, and which constant current is applied to the LED 35 causing it to produce and transmit light to the optical fiber 15 mounted in the laryngoscope handle 14 to and through the Lens 42 for illuminated tracheal intubation.

Figure 14:
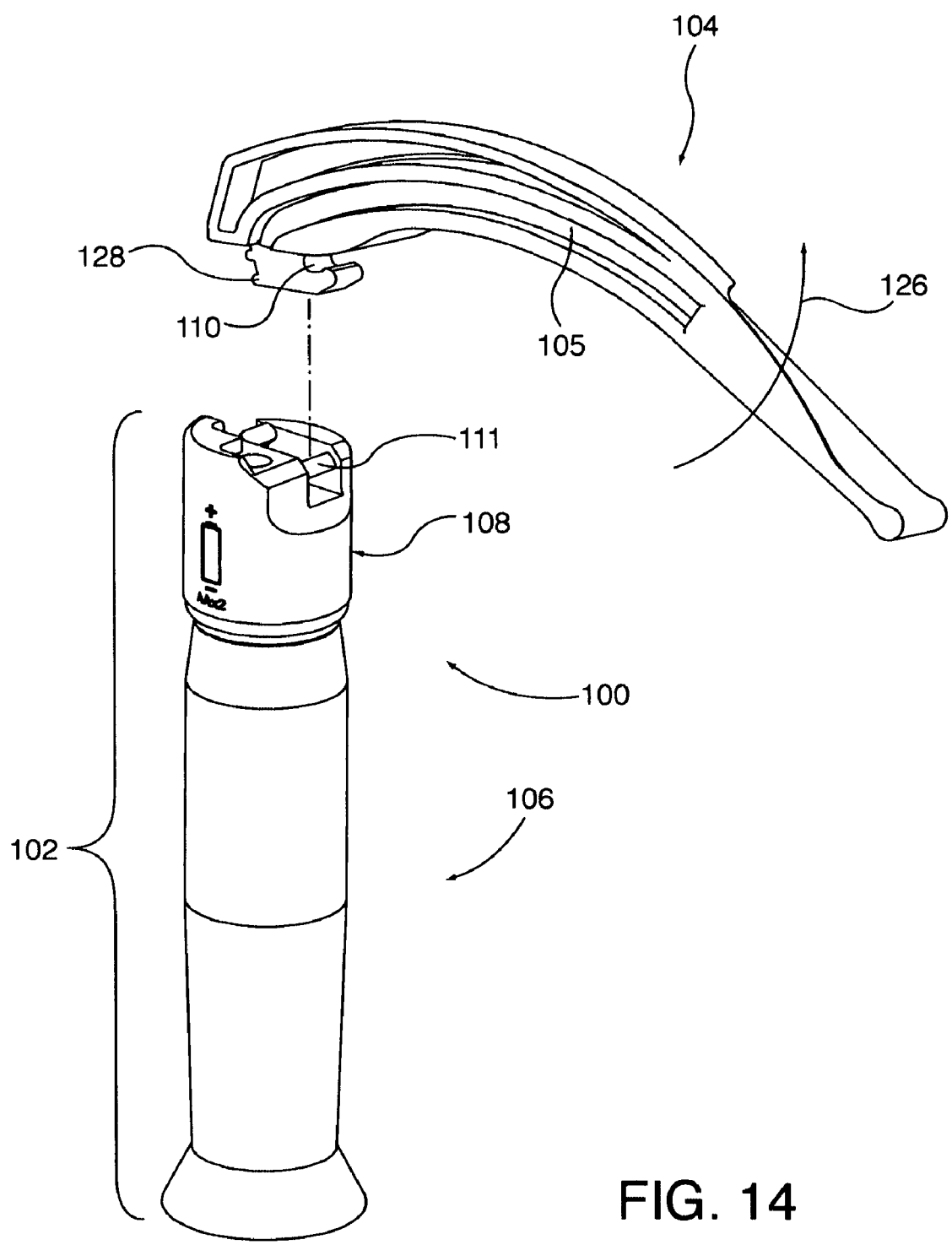
FIG. 14 is a perspective view of a second embodiment of a laryngoscope of the present invention, a second embodiment of a laryngoscope handle apparatus of the present invention, a laryngoscope blade and illustrates the mounting of the blade to the laryngoscope handle apparatus.
Figure 16:
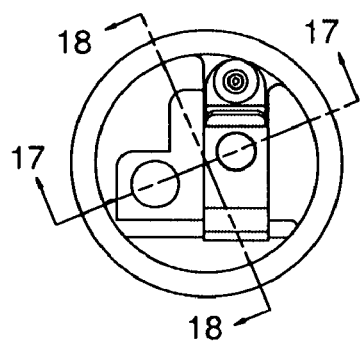
FIG. 16 is a top view of FIG. 15.
Figure 15:
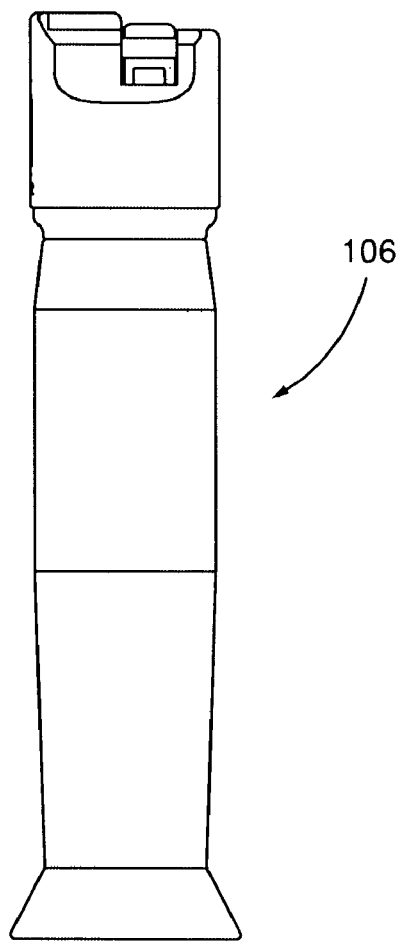
FIG. 15 is a vertical external view of the second embodiment of the laryngoscope handle apparatus of the present invention.

A second embodiment of a laryngoscope embodying the present invention, and also for providing illuminated tracheal intubation, is shown in FIG. 14 and indicated by general numerical designation 100.

The Laryngoscope 100 includes Laryngoscope handle apparatus indicated by general numerical designation 102, and a Laryngoscope blade indicated by general numerical designation 104, and in which blade an optical fiber 105 is mounted in the manner known to the art.

The laryngoscope handle apparatus 102 includes an ergonomic laryngoscope handle indicated by general numerical designation 106, and a head indicated by general numerical designation 108 mounted to the upper end of the ergonomic laryngoscope handle 106.

The laryngoscope blade 104 is provided with an inwardly curved surface 110 for engaging the cylindrical rod 111 provided at the top of the head 108, in the manner known to the art and as indicated by the dashed line in FIG. 14, to mount the laryngoscope blade 104 removably and pivotally to the head 108, and to the laryngoscope handle apparatus 102.

The ergonomic laryngoscope handle 106 includes the hollow rigid inner aluminum cylinder 22 and the generally cylindrical outer soft layer of material 24 shown in FIG. 2 and described above.

Referring generally into FIGS. 17-21, and particularly to FIG. 17, an LED 112 is mounted to a printed circuit board 114, including an LED drive circuit which is connected to the negative battery terminal 116 through the laryngoscope handle apparatus 106, as described in detail below, and which is connected to the positive battery terminal 118 through a normally open electrical switch 120 as described in detail below; the switch 120 includes a plunger 121 and a spring 122.

Figure 17:
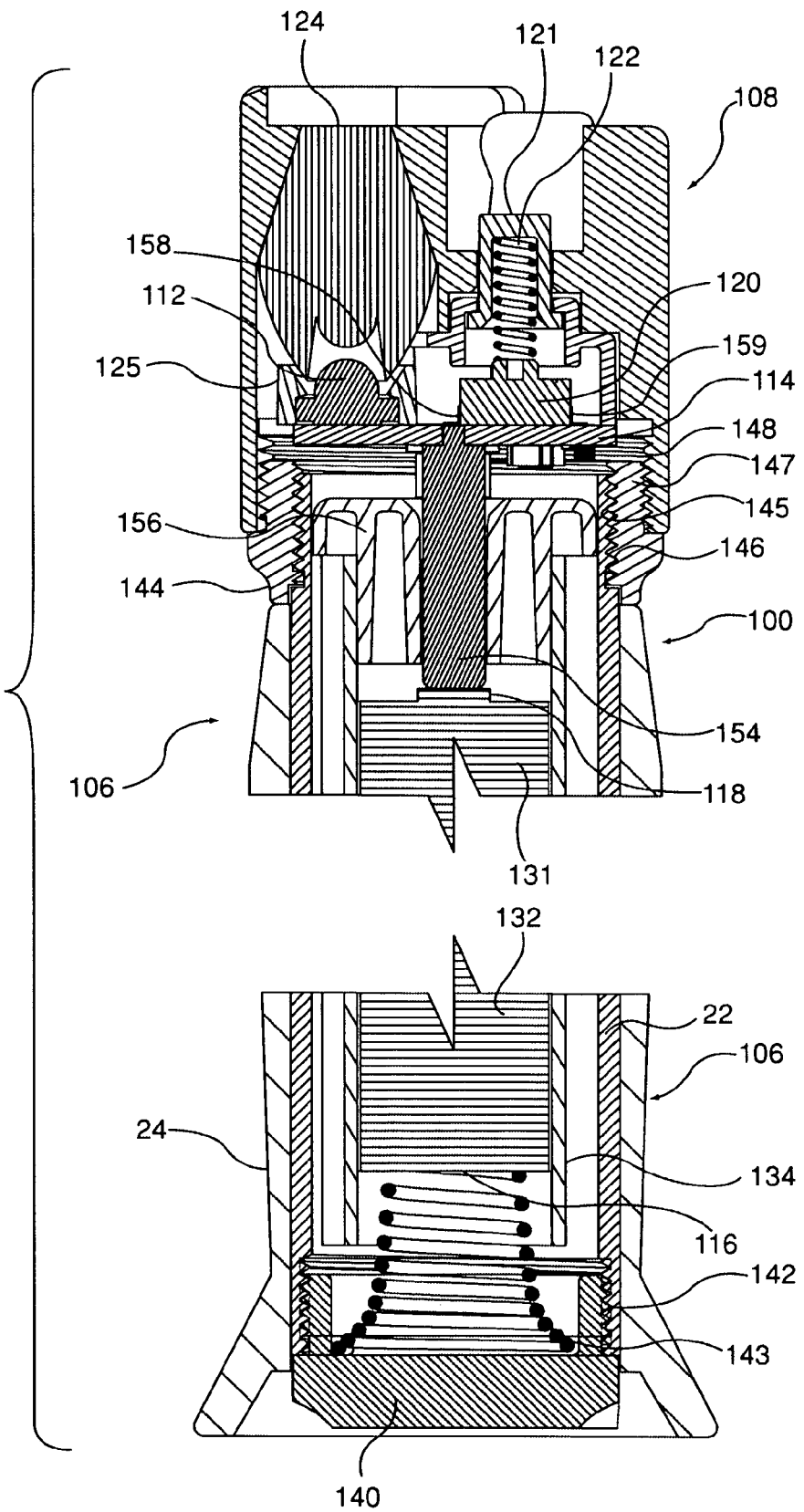
FIG. 17 is a vertical cross-sectional view taken generally along the line 17-17 in FIG. 16 and in the direction of the arrows.

A lens, or total internal reflection collector, 124 is mounted in the head 108 and to the LED as shown in FIG. 17. A generally annular lens spacer 125 may be included to locate the lens 124 relative to the LED 112 in an optically correct position in the manner known to the art.

Figure 20:
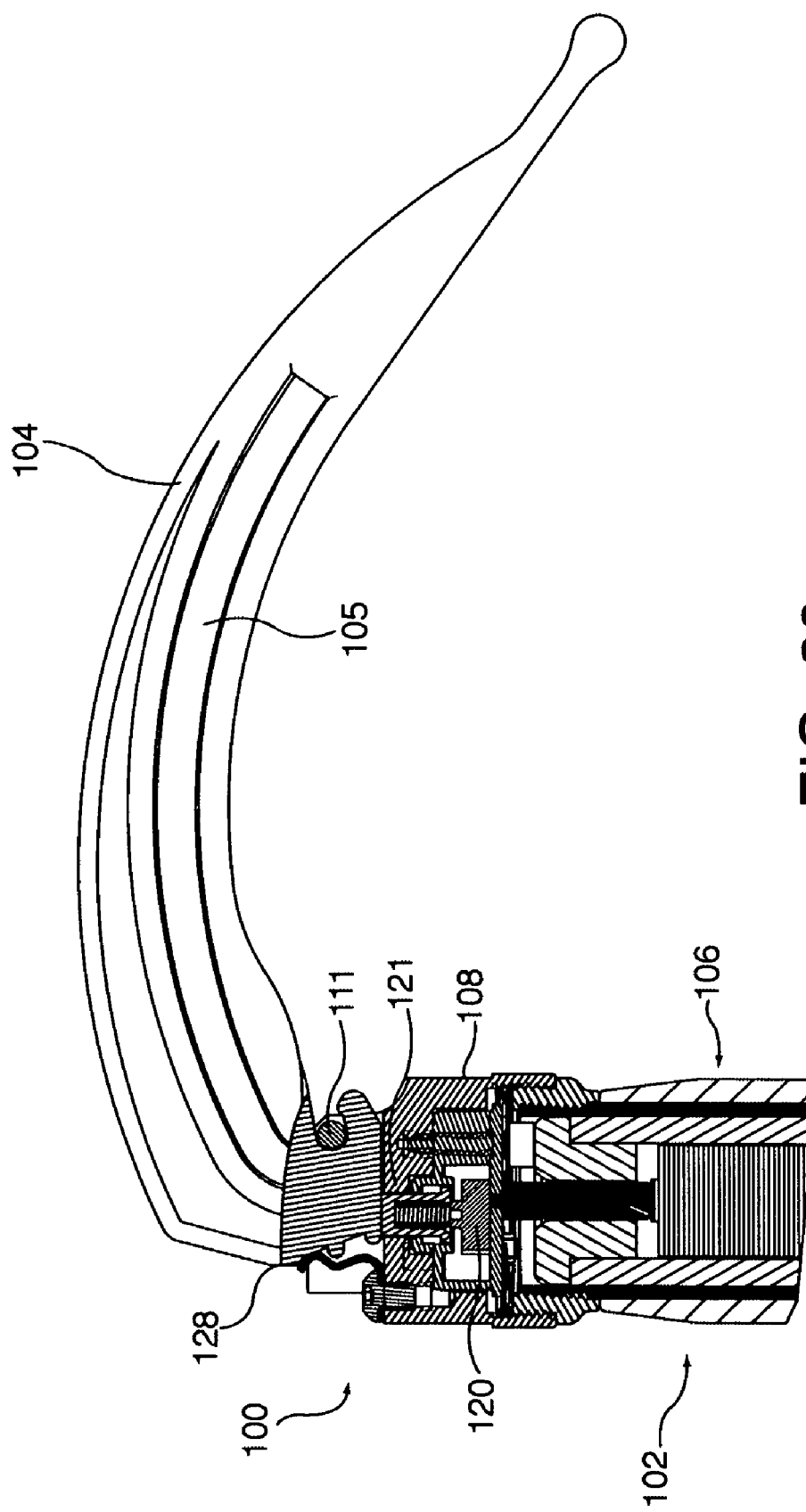
FIG. 20 is an illustration of the mounting of the laryngoscope to the laryngoscope handle apparatus to close the normally open switch to provide illuminated tracheal intubation.

Generally, upon the laryngoscope blade 104, FIG. 14, being mounted pivotally to the laryngoscope handle apparatus 102, as described above, and upon the blade 104 being pivoted away from the handle as indicated by the curved arrow 126 in FIG. 14, and as will be more fully understood with reference to FIG. 20, the base 128 of the blade 104 is pivoted downwardly against the switch plunger 121, FIG. 17, to close the normally open electrical switch 120, and connect the LED drive circuit contained in the printed circuit board 114 to the positive battery terminal 118, FIG. 17.

This connection supplies DC voltage from the batteries 131 and 132, to the LED drive circuit in the printed circuit board 114 which produces and applies constant current, over a broad voltage, to the LED 112 to energize and cause the LED to emit light transmitted through the total internal reflection lens collector 124 to the optical fiber 105, FIG. 14 for illuminated intubation.

Figure 21:
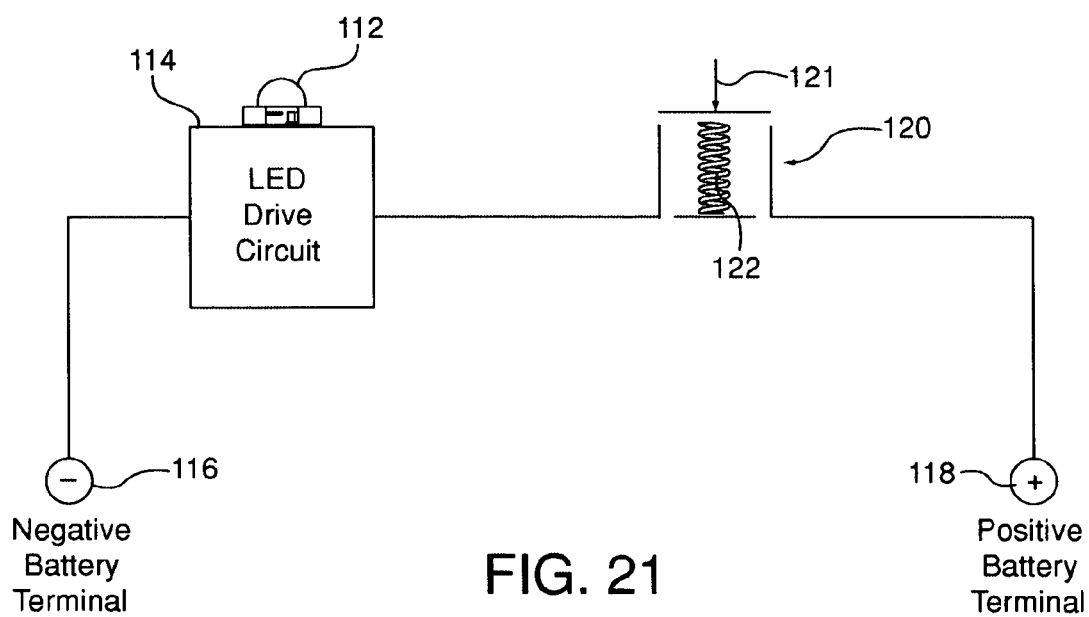
FIG. 21 is a simplified diagrammatical schematic illustrating the normally open positive battery connection to the LED drive circuit.

A diagrammatical schematic of the electrical connection of the LED drive circuit contained in the printed circuit board 114 to the positive and negative battery terminals 116 and 118, upon the normally open electrical switch 120 being closed, is illustrated in FIG. 21.

Referring again to FIG. 17, the batteries 131 and 132 are mounted serially in a cylindrical battery casing 134 and are inserted into the bottom of the handle 106 and held in place therein by an electrically conductive spring 138 and an electric conductive end cap 140.

The lower portion of the rigid inner cylindrical tube 22, FIG. 17, is provided with internal threads 142 which threadedly engage the external threads 143 provided on the end cap 140 to mount and seat the batteries in the handle.

Referring further to FIG. 17, the handle 106 is connected mechanically and electrically to the head 108 by an electrically conductive annular adapter 144. The adapter 144 is provided with internal threads 145 which threadedly engage the external threads 146 provided on the cylinder 22 to mount the adapter electrically and mechanically to the cylinder 22. The adapter 144 is further provided with external threads 147, which threadedly engage the internal threads 148 formed on the lower portion of the head 108. The head 108 is electrically conductive and may be made, for example, of a suitable stainless steel.

Figure 18:
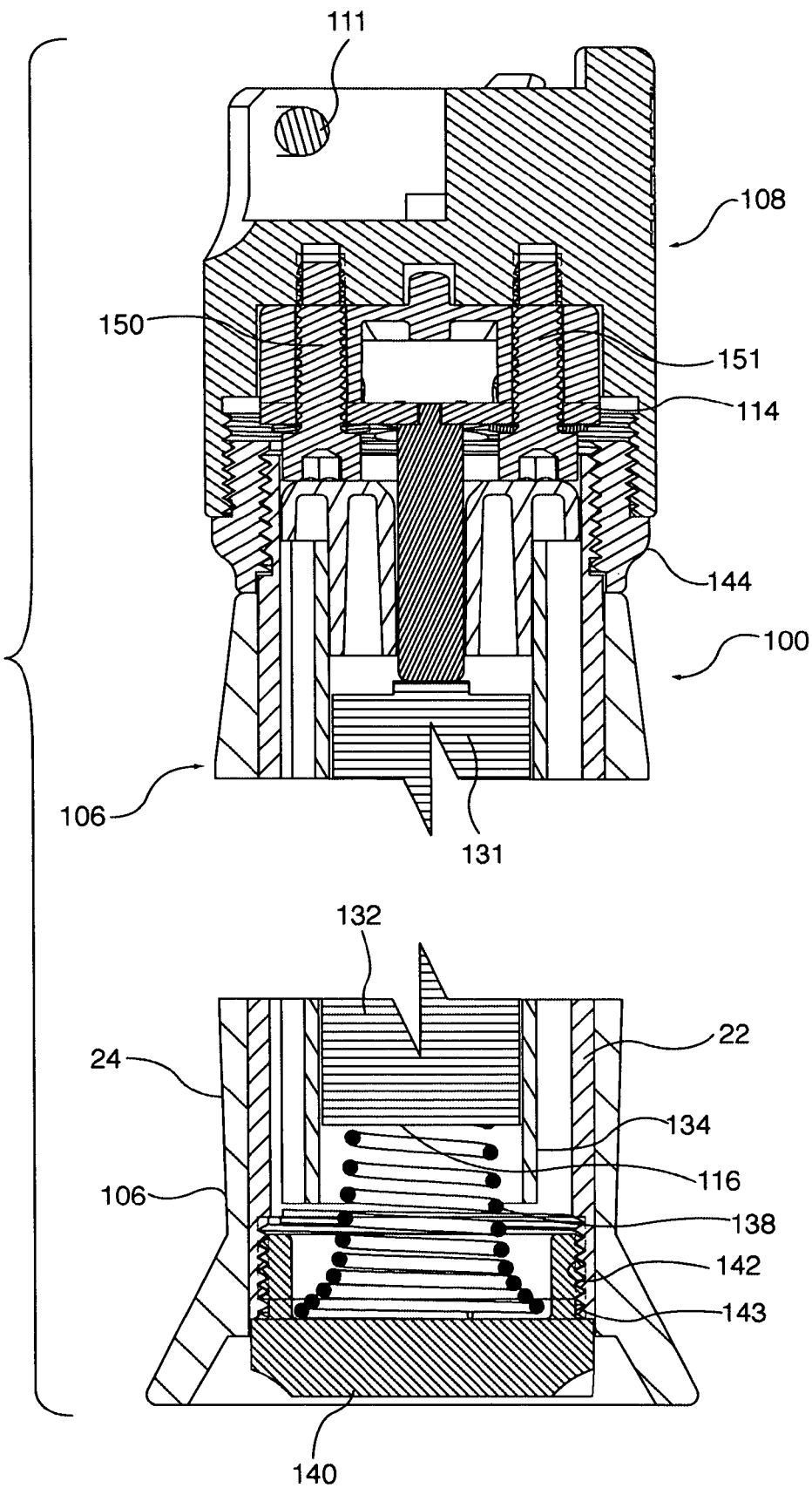
FIG. 18 is a vertical cross-sectional view taken generally along the line 18-18 in FIG. 16 and in the direction of the arrows.

The connection of the LED drive circuit contained in the printed circuit board 114 to the batteries 131 and 132 will be understood particularly with reference to FIG. 18. The negative terminal 116 of the battery 132 is in mechanical and electrical engagement with the electrically conductive compression spring 138, which is in electrical and mechanical engagement with the electrically conductive end cap 140, which in turn is in mechanical electrical engagement with the rigid and electrically conductive inner cylinder 122, of the handle 106, which is in mechanical and electrical engagement with the electrically conductive annular adapter 144, which is in mechanical and electrical engagement with the electrically conductive head 108. It will be understood that the printed circuit board 114 is mounted to the head 108 by a pair of electrical conductive screws or bolts 150 and 151, which extends through holes formed in the printed circuit board 114 and screw into the head 108. The electrically conductive screws 150, 151 mechanically and electrically engage traces, not shown but provided in the printed circuit board 114 in the manner known to the art, to connect the LED drive circuit contained in the printed circuit board 114 to the negative battery terminal 116 through the head, 108, adapter 144, cylinder 22, end cap 140 and the compression spring 138 as described above. Accordingly, it will be understood that the LED drive circuit contained in the printed circuit board 114 is connected to the negative battery terminal 116 through a normally closed negative connection or negative connector circuit.

The connection of the LED drive circuit contained in the printed circuit board 114 to the positive battery terminal 154, through a normally open electrical circuit, is illustrated in FIG. 17. A cylindrical, electrically conductive positive battery contact 154 is mounted perpendicularly and mechanically at the bottom surface of the printed circuit board 114 and includes an upper, reduced in size, cylindrical portion which extends through a hole formed in the printed circuit board, and the upper portion of the positive battery contact 154 may be mounted mechanically to the circuit board 114 such as by soldering. It will be understood that the positive battery contact 154 does not connect directly to the LED drive circuit contained in the printed circuit board 114.

Figure 19:
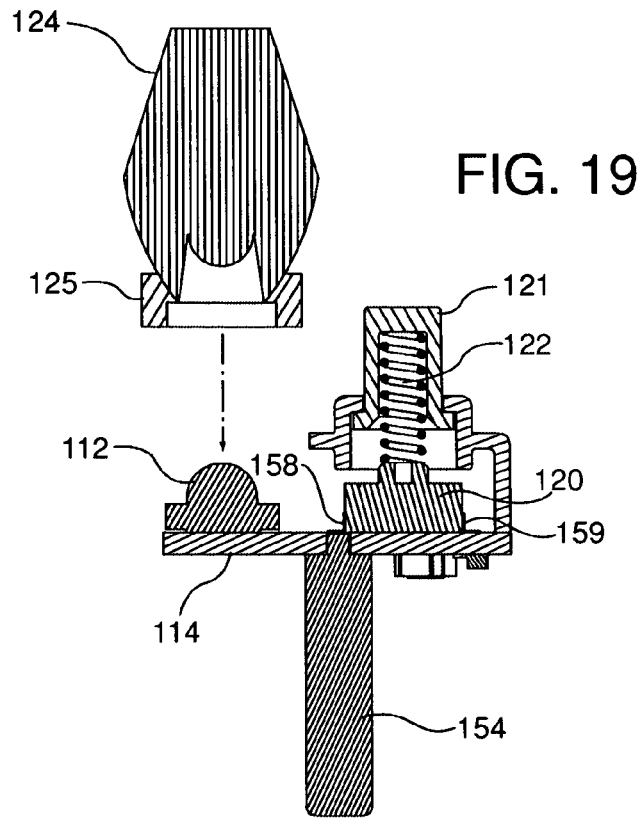

The positive battery contact 154 is spaced and maintained centrally of the handle 106 by a battery contact spacer member 156; the positive battery spacer 156 may be made of a suitable thermoplastic such as acetal co-polymer. The normally open electrical switch 120 includes a first switch terminal 158 and a second switch terminal 159, the switch and switch terminals are also shown in FIG. 19. The switch terminal 158, FIG. 17, is connected to the positive battery contact 154 through a suitable electrical trace provided in the printed circuit board 114 in the manner known to the art. The switch terminal 159 is connected directly to the LED drive circuit contained in the printed circuit board 114 by a suitable electrical trace provided in the printed circuit board 114 in the manner known to the art.

Figure 22:
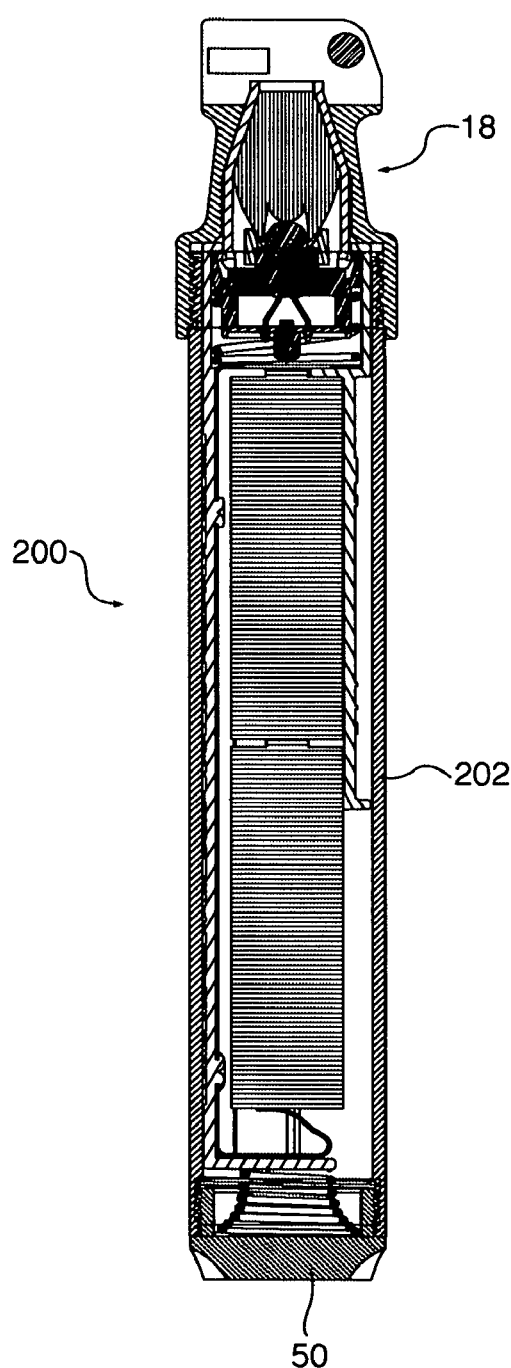
FIG. 22 is a vertical cross-sectional view of a third embodiment of a laryngoscope of the present invention.

Referring again to FIG. 20, upon the Laryngoscope blade 104 being pivoted upwardly, in the direction of the curved arrow 126 in FIG. 14, for the above noted tracheal intubation, the base 128 of laryngoscope blade 104, FIG. 20, is pivoted downwardly and engages the switch plunger 121 forcing it downwardly against the action of the switch spring 122, FIG. 19, interconnecting the switch terminals 158 and 159, in the manner known to the art, which connects the LED drive circuit contained in the printed circuit board 114 to the positive battery terminal 118, FIG. 17 through the positive battery contact 154, the now closed electrical switch 120. It will be understood that the electrical connecting circuit provided by the positive battery contact 154 and the switch 120 is a normally open positive battery connection A third embodiment of a laryngoscope of the present invention is shown in vertical cross-section in FIG. 22 and is identified by general numerical designation 200. Laryngoscope 200 is the same as the first laryngoscope embodiment 10 shown in FIGS. 1-13 and described above, except that the hollow cylindrical metal handle 202 shown in FIG. 22 replaces the ergonomic handle 16 shown in FIG. 1. The handle 202 may be made of a suitable stainless steel and may be knurled to facilitate gripping and handling. The lower inner portion of the handle 202 is provided with internal threads to threadedly engage the external threads on the end cap 50 and the upper portion of the handle is provided with external threads to threadedly engage the internal threads on the head 18 as shown in FIG. 22.

Figure 23:
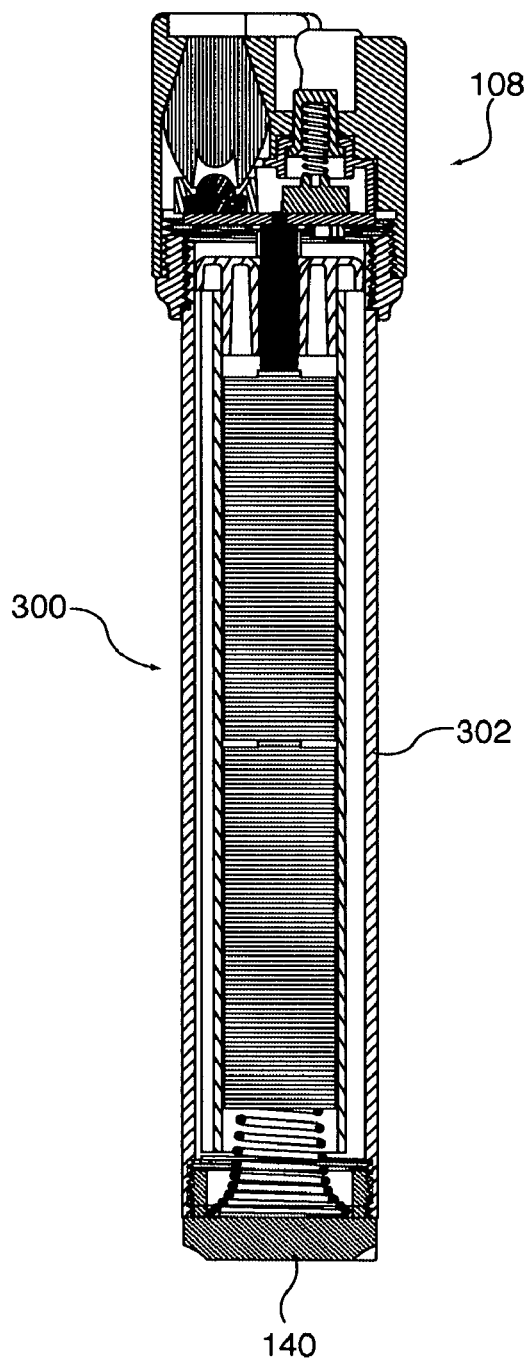
FIG. 23 is a vertical cross-sectional view of a fourth embodiment of a laryngoscope of the present invention.

A fourth embodiment of a laryngoscope of the present invention is shown in vertical cross-section in FIG. 23 and is identified by general designation 300. Laryngoscope 300 is the same as the second laryngoscope embodiment 100 shown in FIGS. 14-21 and described above, except that the hollow cylindrical metal handle 302 shown in FIG. 23 replaces the ergonomic handle 106 shown in FIG. 14. The handle 302 may be made of a suitable stainless steel and may be knurled to facilitate gripping and handling. The lower inner portion of the handle 301 is provided with internal threads to threadedly engage the external threads on the end cap 140 and the upper portion of the handle 302 is provided with external threads to threadedly engage the internal threads on the head 108 as shown in FIG. 23. The metal handle 302 performs the same function as the aluminum cylinder 22 in FIG. 18 in providing part of the normally closed negative connection between the LED drive circuit and the negative battery terminal as described above in laryngoscope 100.

It will be understood by those skilled in the art that many modifications and variations may be made in the present invention without departing from the spirit and the scope thereof.

The invention claimed is:

1. Laryngoscope handle apparatus, comprising:
   an ergonomic handle for containing a DC energy source, wherein said ergonomic handle includes a hollow rigid inner cylinder and a generally cylindrical outer soft layer of material molded around said inner cylinder and having a durometer of about 55 on the Shore A scale, and wherein said layer of soft material includes a generally cylindrical central portion having uniform diametrical cross-section, a first outer portion varying in diametrical cross-section and tapering inwardly at a taper angle A1 and an opposing second outer portion varying in diametrical cross-section and tapering inwardly at a taper angle A2 smaller than said taper angle A1;
   an LED light source;
   an LED drive circuit;
   a lens, wherein said lens is a total internal reflection collector; and
   means for connecting said DC energy source to said LED drive circuit to cause said LED drive circuit to produce and apply constant current to said LED light source which produces and transmits light to and through said lens.

2. The apparatus according to claim 1, wherein said layer of soft material is a synthetic thermoplastic rubber.

3. Laryngoscope handle apparatus, comprising:
   an ergonomic handle for containing a DC energy source wherein said ergonomic handle includes a hollow rigid inner cylinder and a generally cylindrical outer soft layer of material molded around said inner cylinder and having a durometer of about 55 on the Shore A scale, and wherein said layer of soft material includes a generally cylindrical central portion having a uniform diametrical cross-section, a first outer portion varying in diametrical cross-section and tapering inwardly at a taper angle A1 and an opposing second outer portion varying in diametrical cross-section and tapering inwardly at a taper angle A2 smaller than said taper angle A1;
   a head mounted to one end of said ergonomic handle;
   an LED light source mounted in said handle apparatus;
   an LED drive circuit mounted in said handle apparatus and connected to said LED light source;
   a lens mounted in said head and to said LED light source, wherein said lens is a total internal reflection collector; and
   means for connecting said DC energy source to said LED drive circuit to cause said LED drive circuit to produce and apply constant current to said LED light source which produces and transmits light to and through said lens.

4. The apparatus according to claim 3, further comprising a DC energy source disposed in the ergonomic handle, wherein said DC energy source includes a negative terminal and a positive terminal, wherein said means for connecting said DC energy source to said LED drive circuit are normally electrically open means for connecting said DC energy source to said LED drive circuit and include normally closed negative connector means connecting said negative terminal to said LED drive circuit and normally open positive connector means connected to said LED drive circuit and for being closed to connect said DC energy source to said LED drive circuit.

5. The apparatus according to claim 4 wherein said negative connector means include an electrically conductive elongated connector including a first end connected to said negative terminal and a second end including an annular portion surrounding and spaced from said positive terminal and an electrically conductive compression spring mounted intermediate said annular portion and said LED drive circuitry and for normally biasing said positive connector means out of engagement with said positive terminal.

6. The apparatus according to claim 5 wherein said DC energy source includes at least one battery, wherein said apparatus further includes a generally cylindrical casing residing in said ergonomic handle and including a first portion providing a first chamber and a second portion providing a second chamber and including a generally C-shaped inwardly extending seating shoulder intermediate said first chamber and said second chamber, said first chamber for receiving said battery and said second chamber for receiving said LED drive circuit, said first end of said elongated member formed inwardly upon itself to provide a spring for mechanically and electrically engaging said negative terminal and for biasing said battery against said seating shoulder in said second chamber, said annular portion of said elongated member extending inwardly between said first chamber and said second chamber and residing on said seating shoulder, said casing including an upper portion providing a generally central opening through which said lens extends.

7. The apparatus according to claim 4 wherein said head is electrically conductive, wherein said inner cylinder is electrically conductive, wherein said apparatus further includes an electrically conductive adapter mechanically and electrically interconnecting said head and said inner cylinder, wherein said apparatus further includes an electrically conductive end cap mechanically and electrically connected to said inner cylinder and an electrically conductive compression spring intermediate said end cap and said negative terminal and said spring and said end cap mounting said DC energy source in said handle, wherein said LED drive circuit is contained in a printed circuit board, wherein said apparatus further includes at least one electrically conductive screw mounting said printed circuit board mechanically and electrically to said head, and wherein said normally closed negative connector means includes said spring, said end cap, said inner cylinder, said adapter, said head and said screw.

8. The apparatus according to claim 4 wherein said LED drive circuit is contained in a printed circuit board mounted to said head, wherein said apparatus further includes a positive battery contact for being connected to said positive terminal, a normally open electrical switch including a first switch terminal and a second switch terminal, and wherein said first switch terminal is connected electrically to said positive battery contact and wherein said second switch terminal is connected electrically to said LED drive circuit, and wherein upon said switch being closed, said positive terminal is connected to said LED drive circuit, and wherein said normally open positive connector means includes said positive battery contact and said normally open electrical switch.

9. Laryngoscope for providing illuminated tracheal intubation, comprising:
laryngoscope handle apparatus including a head for being mounted to a laryngoscope blade and a hollow cylindrical handle for containing a DC energy source and including a hollow rigid inner cylinder and a generally cylindrical outer soft layer of material molded around said inner cylinder and having an ergonomic shape and a durometer of about 55 on the Shore A scale, and a head mounted to one end of said handle;

a module including at least one LED and a printed circuit board including a LED drive circuit mounted in said laryngoscope handle apparatus, said LED mounted mechanically and electrically to said printed circuit board, wherein said module further includes a generally annular heat sink providing an upper inner annular shoulder and a lower inner annular shoulder separated from said first inner annular shoulder by a cylindrical opening, wherein said printed circuit board is a first circular printed circuit board having a top surface to which said LED is mounted and a bottom surface including an outer annular portion residing on said first inward annular shoulder, said module further including a second printed circuit board having a top surface including an outer annular portion residing on said second inward annular shoulder, said top surface of said second printed circuit board provided with a first electrical trace and a second electrical trace, said module further including a positive connector mounted generally centrally to and extending downwardly from said second printed circuit board, said first printed circuit board further including a positive lead extending downwardly therefrom through said cylindrical opening and connected mechanically to said second printed circuit board and electrically to said first electrical trace which electrically interconnects said positive lead and said positive connector, and said first printed circuit board further including a negative lead extending downwardly therefrom through said cylindrical opening and connected mechanically to said second printed circuit board and electrically to said second trace which electrically interconnects said negative lead and said heat sink;

a total internal reflector collector mounted in said laryngoscope handle apparatus and to said LED;

a normally open connector circuit mounted in said laryngoscope handle apparatus and connected between said DC energy source and said LED drive circuit;

a laryngoscope blade provided with an optical fiber and for being mounted removably and pivotally to said head; and upon said blade being mounted to said head and pivoted away from said handle for tracheal intubation, said blade closing said connector circuit to connect said DC energy source to said LED drive circuit which produces and applies constant current to said LED which emits light which is transmitted to said optical fiber through said total internal reflection collector and which light is transmitted through said optical fiber for illuminated tracheal intubation.

10. The laryngoscope according to claim 9 wherein said module and said total internal reflection collector are mounted moveably in said laryngoscope handle apparatus.

11. The laryngoscope according to claim 9 wherein said module and said total internal reflection collector are mounted fixedly in said laryngoscope handle apparatus.

12. The laryngoscope according to claim 11 wherein said module and said total internal reflection collector are mounted fixedly in said head.

13. The laryngoscope according to claim 9, wherein said heat sink includes an upper portion providing an inward lens cover latching surface, wherein said lens includes an upper portion and a lower portion, wherein said laryngoscope handle apparatus further includes a lens cover for receiving said lens, wherein said lens cover includes an upper portion and a lower portion including a lens latching member, wherein said upper portion of said lens cover is complementary in shape to upper portion of said lens, wherein said upper portion of said lens cover provides an opening through which light emitted from said LED passes, and wherein said lens cover is made of a resilient material to permit said lens latching member to be latched under said lens cover latching surface to latch and mount said lens cover to said heat sink and to mount said lower portion of said lens to said LED.

14. The laryngoscope according to claim 9 wherein said printed circuit board has a top surface and a bottom surface, and wherein said module further includes a positive battery contact and a normally open electrical switch including a first switch terminal and a second switch terminal, wherein positive battery contact is mounted perpendicularly and mechanically at said bottom surface of said printed circuit board and wherein said first switch terminal is connected to said positive battery contact and wherein said second switch terminal is connected to said LED drive circuit.

15. Laryngoscope apparatus, comprising:
a laryngoscope blade;
an ergonomic handle for containing a DC energy source, wherein said ergonomic handle includes a hollow rigid inner cylinder and a generally cylindrical outer soft layer of material molded around said inner cylinder and having a durometer of about 55 on the Shore A scale, and wherein said layer of soft material includes a generally cylindrical central portion having uniform diametrical cross-section, a first outer portion varying in diametrical cross-section and tapering inwardly at a taper angle A1 and an opposing second outer portion varying in diametrical cross-section and tapering inwardly at a taper angle A2 smaller than said taper angle A1;
an LED light source;
an LED drive circuit;
a lens, wherein said lens is a total internal reflection collector; and
means engageable and operable by said blade upon being mounted to said handle for connecting said DC energy source to said LED drive circuit to cause said LED drive circuit to produce and apply constant current to said LED light source which produces and transmits light to and through said lens.

16. The apparatus according to claim 15, wherein said layer of soft material is a synthetic thermoplastic rubber.

17. Laryngoscope handle apparatus, comprising:
a handle containing a DC energy source having a negative terminal and a positive terminal, wherein said DC energy source includes at least one battery;
a head mounted to one end of said handle;
an LED light source mounted in said handle apparatus;
an LED drive circuit mounted in said handle apparatus and connected to said LED light source;
a lens mounted in said head and to said LED light source, wherein said lens is a total internal reflection collector; and
means for connecting said DC energy source to said LED drive circuit to cause said LED drive circuit to produce and apply constant current to said LED light source which produces and transmits light to and through said lens;
wherein said means for connecting said DC energy source to said LED drive circuit are normally electrically open means for connecting said DC energy source to said LED drive circuit and include normally closed negative connector means connecting said negative terminal to said LED drive circuit and normally open positive connector means connected to said LED drive circuit and for being closed by said blade being mounted to said head to connect said DC energy source to said LED drive circuit;
wherein said negative connector means include an electrically conductive elongated connector including a first end connected to said negative terminal and a second end including an annular portion surrounding and spaced from said positive terminal and an electrically conductive compression spring mounted intermediate said annular portion and said LED drive circuitry and for normally biasing said positive connector means out of engagement with said positive terminal; and
wherein said apparatus further includes a generally cylindrical casing residing in said handle and including a first portion providing a first chamber and a second portion providing a second chamber and including a generally semi-circular inwardly extending seating shoulder intermediate said first chamber and said second chamber, said first chamber for receiving said battery and said second chamber for receiving said LED drive circuit, said elongated member including a first portion formed inwardly upon itself to provide a spring for mechanically and electrically engaging said negative terminal and for biasing said battery against said seating shoulder in said second chamber, said annular portion of said elongated member extending inwardly between said first chamber and said second chamber and partially extending over and partially residing on said seating shoulder, said casing including an upper portion providing a generally central opening through which said lens extends.

18. The apparatus according to claim 17, wherein said head is electrically conductive, wherein said inner cylinder is electrically conductive, wherein said apparatus further includes an electrically conductive adapter mechanically and electrically interconnecting said head and said inner cylinder, wherein said apparatus further includes an electrically conductive end cap mechanically and electrically connected to said inner cylinder and an electrically conductive compression spring intermediate said end cap and said negative terminal and said spring and said end cap mounting said DC energy source in said handle, wherein said LED drive circuit is contained in a printed circuit board, wherein said apparatus further includes at least one electrically conductive screw mounting said printed circuit board mechanically and electrically to said head, and wherein said normally closed negative connector means includes said spring, said end cap, said inner cylinder, said adapter, said head and said screw.

19. The apparatus according to claim 17, wherein said LED drive circuit is contained in a printed circuit board mounted to said head, wherein said apparatus further includes a positive battery contact for being connected to said positive terminal, a normally open electrical switch including a first switch terminal and a second switch terminal, and wherein said first switch terminal is connected electrically to said positive battery contact and wherein said second switch terminal is connected electrically to said LED drive circuit, and wherein upon said switch being closed, said positive terminal is connected to said LED drive circuit, and wherein said normally open positive connector means includes said positive battery contact and said normally open electrical switch.

20. Laryngoscope for providing illuminated tracheal intubation, comprising:
laryngoscope handle apparatus including a head for being mounted to a laryngoscope blade and a hollow cylindrical handle for containing a DC energy source;
a module including at least one LED and a printed circuit board including a LED drive circuit mounted in said laryngoscope handle apparatus, said LED mounted mechanically and electrically to said printed circuit board, wherein said module further includes a generally annular heat sink providing an upper inner annular shoulder and a lower inner annular shoulder separated from said first inner annular shoulder by a cylindrical opening, wherein said printed circuit board is a first circular printed circuit board having a top surface to which said LED is mounted and a bottom surface including an outer annular portion residing on said first inward annular shoulder, said module further including a second printed circuit board having a top surface including an outer annular portion residing on said second inward annular shoulder, said top surface of said second printed circuit board provided with a first electrical trace and a second electrical trace, said module further including a positive connector mounted generally centrally to and extending downwardly from said second printed circuit board, said first printed circuit board further including a positive lead extending downwardly therefrom through said cylindrical opening and connected mechanically to said second printed circuit board and electrically to said first electrical trace which electrically interconnects said positive lead and said positive connector, and said first printed circuit board further including a negative lead extending downwardly therefrom through said cylindrical opening and connected mechanically to said second printed circuit board and electrically to said second trace which electrically interconnects said negative lead and said heat sink;

a total internal reflector collector mounted in said laryngoscope handle apparatus and to said LED;

a normally open connector circuit mounted in said laryngoscope handle apparatus and connected between said DC energy source, when installed, and said LED drive circuit;

a laryngoscope blade provided with an optical fiber and for being mounted removably and pivotally to said head; and upon said blade being mounted to said head and pivoted away from said handle for tracheal intubation, said blade closing said connector circuit to connect said DC energy source to said LED drive circuit which produces and applies constant current to said LED which emits light which is transmitted to said optical fiber through said total internal reflection collector and which light is transmitted through said optical fiber for illuminated tracheal intubation.

21. The laryngoscope according to claim 20 wherein said module and said total internal reflection collector are mounted moveably in said laryngoscope handle apparatus.

22. The laryngoscope according to claim 20 wherein said module and said total internal reflection collector are mounted fixedly in said laryngoscope handle apparatus.

23. The laryngoscope according to claim 20 wherein said module and said total internal reflection collector are mounted fixedly in said head.

24. The laryngoscope according to claim 20, wherein said heat sink includes an upper portion providing an inward lens cover latching surface, wherein said lens includes an upper portion and a lower portion, wherein said laryngoscope handle apparatus further includes a lens cover for receiving said lens, wherein said lens cover includes an upper portion and a lower portion including a lens latching member, wherein said upper portion of said lens cover is complementary in shape to upper portion of said lens, wherein said upper portion of said lens cover provides an opening through which light emitted from said LED passes, and wherein said lens cover is made of a resilient material to permit said lens latching member to be latched under said lens cover latching surface to latch and mount said lens cover to said heat sink and to mount said lower portion of said lens to said LED.

25. The laryngoscope according to claim 20 further comprising a DC energy source disposed in the ergonomic handle, wherein said DC energy source includes a positive terminal and a negative terminal, wherein said laryngoscope handle apparatus connects said LED drive circuit to said negative terminal, wherein said printed circuit board has a top surface and a bottom surface, and wherein said module further includes a positive battery contact and a normally open electrical switch including a first switch terminal and a second switch terminal, wherein positive battery contact is mounted perpendicularly and mechanically at said bottom surface of said printed circuit board and is in contact with said positive terminal, wherein said first switch terminal is connected to said positive battery contact and wherein said second switch terminal is connected to said LED drive circuit, and wherein upon said blade pivoted away from said handle, said blade closing said normally open electrical switch to connect said LED drive circuit to said positive terminal.

26. Laryngoscope handle apparatus, comprising:

an ergonomic handle having a DC energy source disposed therein, wherein said DC energy source includes a negative terminal and a positive terminal and wherein said DC energy source includes at least one battery;

a head mounted to one end of said ergonomic handle;

an LED light source mounted in said handle apparatus;

an LED drive circuit mounted in said handle apparatus and connected to said LED light source;

a lens mounted in said head and to said LED light source, wherein said lens is a total internal reflection collector; and means for connecting said DC energy source to said LED drive circuit to cause said LED drive circuit to produce and apply constant current to said LED light source which produces and transmits light to and through said lens;

wherein said means for connecting said DC energy source to said LED drive circuit are normally electrically open means for connecting said DC energy source to said LED drive circuit and include normally closed negative connector means connecting said negative terminal to said LED drive circuit and normally open positive connector means connected to said LED drive circuit and for being closed to connect said DC energy source to said LED drive circuit;

wherein said negative connector means include an electrically conductive elongated connector including a first end connected to said negative terminal and a second end including an annular portion surrounding and spaced from said positive terminal and an electrically conductive compression spring mounted intermediate said annular portion and said LED drive circuitry and for normally biasing said positive connector means out of engagement with said positive terminal; and wherein said apparatus further includes a generally cylindrical casing residing in said ergonomic handle and including a first portion providing a first chamber and a second portion providing a second chamber and including a generally C-shaped inwardly extending seating shoulder intermediate said first chamber and said second chamber, said first chamber for receiving said battery and said second chamber for receiving said LED drive circuit, said first end of said elongated member formed inwardly upon itself to provide a spring for mechanically and electrically engaging said negative terminal and for biasing said battery against said seating shoulder in said second chamber, said annular portion of said elongated member extending inwardly between said first chamber and said second chamber and residing on said seating shoulder, said casing including an upper portion providing a generally central opening through which said lens extends.

27. The apparatus according to claim 26, wherein said head is electrically conductive, wherein said inner cylinder is electrically conductive, wherein said apparatus further includes an electrically conductive adapter mechanically and electrically interconnecting said head and said inner cylinder, wherein said apparatus further includes an electrically conductive end cap mechanically and electrically connected to said inner cylinder and an electrically conductive compression spring intermediate said end cap and said negative terminal and said spring and said end cap mounting said DC energy source in said handle, wherein said LED drive circuit is contained in a printed circuit board, wherein said apparatus further includes at least one electrically conductive screw mounting said printed circuit board mechanically and electrically to said head, and wherein said normally closed negative connector means includes said spring, said end cap, said inner cylinder, said adapter, said head and said screw.

28. The apparatus according to claim 26, wherein said LED drive circuit is contained in a printed circuit board mounted to said head, wherein said apparatus further includes a positive battery contact for being connected to said positive terminal, a normally open electrical switch including a first switch terminal and a second switch terminal, and wherein said first switch terminal is connected electrically to said positive battery contact and wherein said second switch terminal is connected electrically to said LED drive circuit, and wherein upon said switch being closed, said positive terminal is connected to said LED drive circuit, and wherein said normally open positive connector means includes said positive battery contact and said normally open electrical switch.

* * * * *

UNITED STATES PATENT AND TRADEMARK OFFICE
CERTIFICATE OF CORRECTION

PATENT NO. : 7,771,350 B2
APPLICATION NO. : 11/255323
DATED : August 10, 2010
INVENTOR(S) : Geist et al.

Page 1 of 1

It is certified that error appears in the above-identified patent and that said Letters Patent is hereby corrected as shown below:

On the Title Page, Item (74), under "Attorney, Agent, or Firm", in Column 2, Line 1, delete "Mosier" and insert -- Moser --, therefor.

In Column 4, Line 25, delete "M" and insert -- AA --, therefor.

Signed and Sealed this
Nineteenth Day of April, 2011

David J. Kappos
*Director of the United States Patent and Trademark Office*